(12) United States Patent
Jasch

(10) Patent No.: US 8,840,921 B2
(45) Date of Patent: Sep. 23, 2014

(54) PATCH PRODUCTION TECHNOLOGY

(75) Inventor: Ingolf Jasch, Solingen (DE)

(73) Assignee: UCB Pharma GmbH, Monheim (DE)

( * ) Notice: Subject to any disclaimer, the term of this patent is extended or adjusted under 35 U.S.C. 154(b) by 314 days.

(21) Appl. No.: 13/142,576

(22) PCT Filed: Dec. 22, 2009

(86) PCT No.: PCT/EP2009/009207
§ 371 (c)(1),
(2), (4) Date: Jun. 28, 2011

(87) PCT Pub. No.: WO2010/075992
PCT Pub. Date: Jul. 8, 2010

(65) Prior Publication Data
US 2011/0268786 A1    Nov. 3, 2011

(30) Foreign Application Priority Data
Dec. 29, 2008   (EP) ..................................... 08173017

(51) Int. Cl.
*A61K 9/70* (2006.01)
*A61K 31/38* (2006.01)
*A61F 13/02* (2006.01)
*B26D 7/10* (2006.01)
*B26D 3/08* (2006.01)
*B26F 1/38* (2006.01)

(52) U.S. Cl.
CPC ................ *A61K 9/703* (2013.01); *A61F 13/02* (2013.01); *A61F 13/0276* (2013.01); *B26D 7/10* (2013.01); *B26D 3/085* (2013.01); *B26F 1/384* (2013.01)
USPC .......................................... 424/449; 514/438

(58) Field of Classification Search
CPC ... A61K 9/7084; A61K 9/7023; A61K 9/703; A61K 9/7038; A61K 9/7069; C07D 333/08; C07D 333/10; B29C 65/18; B29C 65/02; B29C 66/40
USPC .......................................... 424/449; 514/438
See application file for complete search history.

(56) References Cited

U.S. PATENT DOCUMENTS

| | | | |
|---|---|---|---|
| 4,573,996 A | 3/1986 | Kwiatek et al. | |
| 4,655,768 A * | 4/1987 | Marecki et al. | 424/448 |
| 4,695,277 A | 9/1987 | Lauk | |
| 4,849,224 A * | 7/1989 | Chang et al. | 424/434 |
| 5,405,486 A | 4/1995 | Sablotsky et al. | |
| 5,662,925 A * | 9/1997 | Ebert et al. | 424/447 |
| 5,879,701 A * | 3/1999 | Audett et al. | 424/448 |
| 5,965,154 A * | 10/1999 | Haralambopoulos | 424/449 |
| 6,159,497 A * | 12/2000 | LaPrade et al. | 424/448 |
| 6,884,434 B1 * | 4/2005 | Muller et al. | 424/487 |

FOREIGN PATENT DOCUMENTS

| | | |
|---|---|---|
| CA | 1 252 360 | 4/1989 |
| DE | 34 30 250 C1 | 4/1986 |
| EP | 0 013 606 A | 7/1980 |
| EP | 1 325 742 A | 7/2003 |
| FR | 929 456 A | 12/1947 |
| WO | WO 03/092677 A | 11/2003 |
| WO | WO 2007/147556 A | 12/2007 |
| WO | WO 2008/048829 A | 4/2008 |
| WO | WO 2009/009651 A | 1/2009 |

OTHER PUBLICATIONS

The Merck Manual—Restless Leg Syndrome, obtained online at: www.merckmanuals.com, downloaded online on Jul. 30, 2013, pp. 1-2.*
The Merck Manual—Parkinson's Disease, obtained online at: www.merckmanuals.com, downloaded online on Jul. 30, 2013, pp. 1-7.*
The Merck Manual—Fibromyalgia, obtained online at: www.merckmanuals.com, downloaded online on Jul. 30, 2013, pp. 1-3.*
The Merck Manual—Depression, obtained online at: www.merckmanuals.com, downloaded online on Jul. 30, 2013, pp. 1-9.*
www-materials.eng.cam.ac.uk, obtained online at: http://www-materials.eng.cam.ac.uk/mpsite/properties/non-IE/strength.html, downloaded on Aug. 4, 2013.*

* cited by examiner

*Primary Examiner* — Abigail Fisher
(74) *Attorney, Agent, or Firm* — McDonnell Boehnen Hulbert & Berghoff LLP

(57) ABSTRACT

The invention relates to a transdermal patch with a release liner film, an active substance layer with the active substance rotigotine, and/or one of its pharmacologically acceptable salts, and a carrier layer, wherein the active substance layer is placed between the release liner film and the carrier layer. The invention further relates to a process for manufacturing of a transdermal patch, as well as a tool for producing a patch of this type.

19 Claims, 8 Drawing Sheets

18

PATCH PRODUCTION TECHNOLOGY

This application is a US national phase of International Application No. PCT/EP2009/009207 filed on 22 Dec. 2009, the disclosure of which is incorporated herein by reference in its entirety.

The invention relates to a transdermal patch with a release liner film, an active substance layer, with the active substance rotigotine, and/or one of its pharmacologically acceptable salts, and a carrier layer, wherein the active substance layer is placed between the release liner film and the carrier layer. The invention further relates to a process for manufacturing of a transdermal patch, as well as a tool for producing a patch of this type.

BACKGROUND

Transdermal patches are used for the application of drugs through the skin. After sticking a transdermal patch onto the skin, a drug suitable for this application continuously enters the systemic bloodstream in a direct way, i.e. by bypassing the gastrointestinal tract and the first liver passage, whereby e.g. gastric intolerance and/or the early hepatic 'first-pass' effect (decomposition in the liver) of certain substances after oral administration is avoided. Examples of this include nicotine patches, hormone patches and pain-relieving patches, as well as transdermal patches for treatment of Parkinson's disease, or for treatment of 'restless legs'. Therapeutic patches of this type can contain the dopaminergic active substance rotigotine. Inter alia, it is suitable for treating Parkinson's disease, and for therapy on restless legs, and corresponding transdermal patches are already used in some countries. Medical uses of rotigotine or pharmaceutical forms containing rotigotine are described, for example, in WO 2005/92331, WO 2005/009424, WO 2007/147556, WO 03/92677, as well as WO 2005/63237.

A preferred embodiment of a transdermal patch known in the prior art consists of an active substance layer, a carrier layer and a release liner film. Patches designed in this way are generally punched out of an large-area laminate. After this punching, the active layer is open on the peripheral separating edges, i.e. is not covered by films.

A possible manufacturing of rotigotine patches, which correspond to the above-mentioned embodiment, is described in WO 02/089778 and WO 04/012730, for example. In the process, the active substance rotigotine is contained in a non-crystalline form in a layer containing silicone adhesive. Before introducing rotigotine in the adhesive layer, rotigotine is dissolved in a solvent, and the solvent containing adhesive, loaded with the active substance, is applied in a subsequently continuous coating process on a release liner film, a polyester film, also denoted as a 'release liner' or 'protective film', and the solvent is removed by heating in a drying channel. After the drying process, a carrier layer, which is impermeable for the active substance, is laminated onto the remaining open interface of the rotigotine containing adhesive layer. The laminate manufactured in this way is subsequently divided in individual patches by mechanical separation.

The separating edges between the individual patches are conventionally created by mechanical separation, for example, by cutting or punching through. Additionally, the release liner film can also be provided with an S-shaped cut, the so called 'S-cut'. This cut facilitates a removal of the release liner film from the patch, in order to stick the patch with its rotigotine containing adhesive layer onto the skin of a patient. On one hand, the S-cut can be realised as a continuous cut along the whole patch, or as a 'predetermined breaking point' in the form of specific weakening of the release liner film along an S-cut line. In addition to the above-described form, this 'cut' or 'predetermined breaking point' can comprise other forms, such as the form of a straight or zigzag line. A possible manufacturing process for a transdermal patch is for example described in detail in WO 04/012730, as example 1, beginning on page 14.

However, when the patch created in this way is stored at room temperature, there is a risk that in the active substance layer rotigotine crystal formation occurs in the region of the separating edges, and spread, originating from the edges of the patch or the S-cut of the release liner film in the direction of the inside of the active substance layer, thus away from the corresponding edge, but also along the edge. FIG. 1 shows a separating edge 18 of a patch containing rotigotine, from which crystals 20 are spreading into the active substance layer 14. Rotigotine crystals can form different polymorphs, which can occur alone as well as in a mixture (e.g. form I and form II). In general, the resulting crystals form a thermodynamically stable polymorph II ('form II') of rotigotine. The formation of a crystalline polymorph of this type is undesired in a patch formulation; efforts are therefore made to avoid crystallisation. For this purpose, in some cases up to now, a continuous cooling of the patch is implemented, in order to inhibit the growth of the crystals. However, this requires high logistic effort and expenditure in order to maintain the cold chain from the manufacturing of the patch until its application on patients, and is very difficult to implement in some countries. In addition, the assistance of each patient is required, and therefore the application is more difficult for the patient.

Such a crystallisation of the active substance in the region of the matrix edges, which are open in relation to the environment, also represents a problem for patches with different active substances. This particularly applies to silicone-based patches, whose matrix has a higher permeability for water vapour and oxygen, and for lipophilic, particularly poorly water soluble active substances.

DESCRIPTION OF THE INVENTION

The object of the present invention is therefore to develop a transdermal patch, in which the development of crystals in the active substance layer is impeded and avoided, as far as possible.

The object of the invention is achieved by a transdermal patch, comprising a release liner film, an active substance layer comprising a polymer layer, containing a poorly water soluble active substance, and a carrier layer, wherein the active substance layer is placed between the release liner film and the carrier layer, and wherein the release liner film and/or the carrier layer comprise/s at least one thermally effected peripheral separating edge, which defines at least one peripheral edge of the patch. In a preferred embodiment of the invention, the release liner film and the carrier layer are thermally connected to each other over a length of at least 70%, preferably over the whole length of the peripheral separating edges, in such a way that they can be detached from each other, particularly in such a way that the active substance layer is be closed or sealed thereby.

During administration of the patch, before application onto the skin of the patient, the release liner film is removed, and is therefore easily detachable from the typically self-adhesive active substance layer. The release liner film represents a protective layer for the active substance and the active substance layer containing the active substance when it is applied on the active substance layer. During manufacturing of the patch, the release liner film preferably serves as a carrier for the active substance layer, due to its physical characteristics (such as dimensional stability and tear-resistance under tensile loads). The release liner film also ensures that the active substance remains in the active substance layer in a desired high concentration during storage, and does not volatilise before application of the patch. The release liner film therefore provides a protective function as well as a sealing function for the active substance layer, and can be removed before application of the patch.

The active substance layer contains an active substance, which is suitable for transdermal administration due to its physicochemical characteristics. In general, suitable active substance candidates are lipophilic and only to a limited extent water soluble. If the active substance layer absorbs moisture during storage, for example this is possible in the presence of hygroscopic excipients, the limit of solubility of the lipophilic active substance in the patch can be exceeded, with the consequence of crystal nucleation and crystal growth. This risk is particularly distinct for lipophilic active substances with poor water solubility. In this application active substances, which have a water solubility of maximal 1 mg/ml at a pH of 7 at 15° C., are understood by 'poorly water soluble active substances'. Examples of active substances of this type are estradiol, buprenorphine, fentanyl, norethindrone acetate, and particularly rotigotine and its salts. Advantageously, the active substance e.g. rotigotine is essentially in the form of the free base and in 1-20 wt% present in the active substance layer.

It is conceivable that the active substance layer quasi serves as adhesive layer for the patch. However, it is also possible that a separate adhesive substance layer, which does not provide an adhesive function, and an additional adhesive layer are present.

The carrier layer can also be denoted as a backing layer and is impermeable to the active substance. The backing layer protects the active substance from volatilising when it is in an affixes state, and at the same time serves as a carrier layer for the active substance, after the release liner film has been removed from the patch. Both the release liner film and the carrier layer are preferably in film form.

The release liner film and/or the carrier layer comprise/s at least one separating edge, which defines one peripheral edge of the patch (subsequently 'peripheral separating edge') and which is thermally effected. In a preferred embodiment, at least approximately 60%, 70%, 75%, 80%, 90%, 95% or 99% of the total length of the separating edge of the peripheral edge of the patch are thermally effected. Particularly preferred embodiment, all peripheral separating edges of the patch are completely thermally effected.

In this application, 'thermally effected' usually means that a certain process described in more detail in this application is carried out essentially by using warmth or heat. For example, a separating edge can essentially be created by the effect of warmth or heat, for example by using a heated wire, a hot punch etc. In another example the detachable connection of the peripheral separating edges can essentially be created by the effect of warmth or heat, for example, by welding, thermal caulking and/or thermal joining. In one embodiment, the detachable connection is created by welding. In one example, the detachable connection peripheral separating edges of the release liner film and the carrier layer is essentially created by the effect of warmth or heat, for example, by welding.

The thermally effected and detachable connection of the peripheral separating edges is usually carried out without use of adhesives applied between the release liner film and the carrier layer. In another example, the thermally effected and detachable connection of the peripheral separating edges is typically carried out without the use of non-metallic materials, which connect the release liner film and the carrier layer by surface adhesion (adhesion) and internal strength (cohesion), and which are applied between the release liner film and the carrier layer.

The thermal effecting can take place for example by welding, thermal caulking and/or thermal joining. In one embodiment, the thermal effecting is carried out by welding.

'And/or' means that at least one of the release liner film and the carrier layer comprises a thermally effected separating edge. A separating edge in the context of the present invention can serve on one hand for separation of the patch, and can thus form the peripheral edge of the patch or parts thereof. Furtheron a separating edge can be understood as a separating edge within the edge of the patch, thus a cut on a layer of a separated patch, or a well-directed weakening of one of the layers ('predetermined separating edge' or 'predetermined breaking edge (point)'). On one hand, the separating edge can therefore be a peripheral edge, where a patch is separated from another patch or a blank, on the other hand the separating edge can be a predetermined separating edge which serves for disconnecting a layer e.g. the release liner film for use of the patch. 'Separating' is thus to be understood as quantitative parting and thus the counterpart to 'joining'.

Preferably, the release liner film and the carrier layer are thermally connected to each other at least along one of the peripheral separating edges of the patch, and in such a way that they can be detached from one another. It is particularly preferred that they are connected to each other in such a way that the active substance layer is sealed. In a preferred embodiment, the release liner film and the carrier layer are thermally connected at least along 60%, 70%, 75%, 80%, 90%, 95% or 99% of the total length of the peripheral separating edges, and are connected to each other in such a way that they can be detached from one another.

A continuous 'peripheral separating edge' along the periphery of the patch, for example, in the case of a circular or ellipsoidal patch, can here be considered as several separating edges, in which the transitions between the individual separating edges are continuous.

It is particularly preferred that the release liner film and the carrier layer are thermally connected to each other over the whole length of the peripheral separating edge, in such a way that they can be detached from each other, so that the thermal connection of the release liner film and the carrier layer along the peripheral separating edge encases the active substance layer along this peripheral separating edge. In such a case, the active substance layer can essentially be cut off from the environment and is therefore sealed. The term 'essentially cut off from the environment' means that the gas and active substance exchange between the active substance layer and the patch environment, in contrast to the process known in the prior art, is also eliminated in the region of the edges, insofar as it results from the material characteristics of the carrier and release liner film. Typically, carrier films and release liner films are used, which do not permit permeation of the active substance, and only permit limited gas exchange.

Since the release liner film and the carrier layer are connected to each other in such a way that they can be detached from one another, this means that the bond between both layers is strong enough so that the release liner film sticks to the carrier layer, and is, after manufacturing and during transport and storage, connected to it along the peripheral separating edge via a sealing rim, but both layers, however, during conventional use of the patch can be detached from each other by removing the release liner film, i.e. that neither the release liner film nor the carrier layer are destroyed during removal of the release liner film from the carrier layer. For this purpose the pressure exerted by the tools used for the thermal manufacturing, as well as the width of the sealing rim which results from the thermal manufacturing are adjusted, depending on the respective conditions in the patch, such as thickness and material of the carrier layer, matrix and release liner layer. For example, the sealing rim connecting the release liner film and the carrier layer can have a width of 50-1000 μm, particularly 100-300 μm.

In order to facilitate a displacement of the active substance containing matrix from the area of the sealing rim during the thermal manufacturing of the peripheral cutting line, the active substance matrix advantageously includes a polymer, which has favourable flow properties and a low surface tension. Silicone-based polymers, particularly pressure sensitive polyorganosiloxane adhesives, such as dimethylsiloxane, are fulfilling these requirements to a certain extent, since they, due to their visco-elastic properties, can easily displaced from the area of the sealing rim. This is particularly the case in a preferred embodiment, wherein the materials of the release liner film and carrier layer are siliconised. Preferably the active substance layer has a thickness of 35-120 μm, particularly preferred 40-80 μm, and most particularly preferred 45-60 μm. In a preferred embodiment of the invention, the displacement of the active substance matrix from the provided peripheral separating edges takes place during the thermal separation step. However, it is also conceivable that in a first step a separating edge contour is given by application of pressure, and the thermally effected separation and sealing takes place on the previously effected separating edge contour in a second step. This two-stage process can be particularly advantageous if the active substance is thermally unstable, and is supposed to be displaced in advance from the to be thermally effected area of the cutting edge, and/or if it is very difficult to displace the active substance matrix from the area of the sealing rim in a single processing step.

In the hydrophobic, preferably silicone-based, adhesives, in addition to the active substance, further excipients can also be included, such as, for example, antioxidants such as sodium bisulphate or alpha-tocopherol, penetration enhancers or crystallisation inhibitors such as polyvinylpyrrolidone (e.g. Kollidon®, BASF AG), polyethylene glycol, polypropylene glycol, glycerol and glycerol fatty acids, as well as copolymers of vinyl acetate with ethylene or PVP.

Advantageously, at least the release liner film comprises a weakened and/or at least partially broken region as a predetermined breaking edge, which can be particularly used as an opening aid for the patch. During the use of the patch, a predetermined separating edge of this type serves to separate the release liner film into two parts along a defined edge. For this purpose, the release liner film can be weakened, without, in the case of a thermal bond between the carrier layer and the release liner film, impairing the sealing of the active substance layer outwards. A partial break of the release liner film along the predetermined separating edge of the release liner film can be calculated in such a way that the sealing effect of the active substance layer remains controlled. The weakened and/or at least partially broken region forms a predetermined separating edge, which preferably does not define any peripheral edge of the patch, but rather runs generally along a path on the patch. Typically the predetermined separating edge runs in the plane of extension of the patch along a straight line.

In a preferred embodiment, the release liner film and the carrier layer are made of the same material. Examples for such materials are polyethylenes, polypropylenes as well as polyethylene terephthalate. An advantage of making the release liner film and the carrier layer from the same material is, for example, that the thermal characteristics regarding their stability as well as the sealing characteristics of the release liner film and the carrier layer are equal, apart from possible varying strengths of the individual layers. This leads to simplified processability, in particular a thermally effected peripheral separating edge can be created for both layers, which runs equally for both layers. Preferably, the release liner film and carrier layer are made of a material, whose melting temperature lies in a temperature range, in which the active substance contained in the patch still does not assume any thermal/chemical decomposition or conversion.

In a preferred embodiment, the release liner film and/or the carrier layer comprises a predefined strength or thickness for control of a gas flow through this layer. Depending on the material the release liner film and/or the carrier layer are made of, each of these layers can facilitate a certain gas exchange between the active substance layer and the environment. Typical strengths of the release liner film are approximately 50-150 μm, and for the carrier layer, between approximately 15 μm and approximately 30 μm. A greater strength of layers leads to a reduced gas exchange. When selecting the strength of the layer for regulation of the gas exchange, the porosity of the material of the respective layer is also to be considered which is also preferably predefined, and particularly preferably, is equal for the release liner film and carrier layer. In addition, it is also conceivable that the material of the carrier layer and/or the release liner film is adapted to a desired level of gas flow.

In a process according to the invention for manufacturing of a transdermal patch, an active substance layer, e.g. with rotigotine and/or one of its pharmacologically acceptable salts, is located between a release liner film and a carrier layer, whereby the release liner film and/or the carrier layer of the patch is provided with at least one thermally effected peripheral edge, in order to avoid crystallisation in the region of this separating edge. Preferably, the release liner film and/or the carrier layer of the patch are provided with several peripheral separating edges which are thermally effected along their whole length.

'And/or' means that at least one of the release liner film and the carrier layer of the patch is provided with at least one thermally effected peripheral separating edge. Due to the separating edge being thermally effected, both crystallisation nuclei as well as nuclei of other types can be suppressed or destroyed. In this way, the development of crystals can already be particularly avoided during manufacturing of the patch.

In a preferred process, the release liner film and the carrier layer are thermally connected to each other simultaneously along the peripheral separating edges, over a length of at least 70% of the peripheral separating edges, and preferably over the whole length of the peripheral separating edges. This can take place particularly in such a way that the active substance layer is sealed by means of the layers which are thermally connected to each other. Preferably, it is possible that the peripheral edge at the same time forms a sealing rim between the carrier layer and the release liner film. The connection of the release liner film to the carrier layer along the peripheral edge essentially takes place during the same procedure, which also realises the peripheral edge itself. It is possible, for example, that by using a pair of opposing, heatable rollers or similar tools, on one hand, a peripheral separating edge is thermally effected, and on the other hand, the release liner film and the carrier layer are thermally connected to each other. The release liner film and the carrier layer are connected to each other in such a way that they are subsequently detachable from each other, i.e. that the release liner film can be removed from the carrier layer, without one of both layers having to be destroyed.

Preferably, the release liner film is thermally weakened and/or at least partly broken in an area of a predetermined breaking edge, which can be particularly used as an opening aid for the patch. The predetermined separating edge, which can be used as an opening aid for the patch, lies in the inside of the patch, i.e. within the encompassing edge, which can be formed by a thermally effected peripheral separating edge. In the case of the thermally weakened and/or at least partly broken predetermined separating edge, this can for example be an opening aid corresponding to the so-called S-cut.

In the process, at least one of the thermal treatments is carried out above a melting temperature of the respective active substance crystals. In the process, the thermal treatments describe on one hand, the provision of the patch with at least one thermally effected separating edge, and on the other hand, the connection of the release liner film to the carrier layer along the peripheral separating edge. In the example of rotigotine as an active substance in the active substance layer, the melting point of the corresponding higher melting rotigotine crystals ('form II') is 97° C.±2° C. In order to keep the cutting tools free from crystal nuclei, it is therefore preferred to bring these to a higher temperature than the melting point of the respective active substance crystals, in the case of rotigotine for example to at least 100° C., preferably to over 110° C., or over 120° C.

In addition, the temperature selected must be high enough to guarantee thermal manufacturing of the cutting edges and preferably a fusion of the release liner film with the carrier layer. The required temperatures depend on the type of materials used for the release liner film and the carrier layer, and are in the range e.g. for polyethylene films of approximately 100-120° C. and for polypropylene films approximately 165° C. and above, as well as ca. 260° C. and above for polyethylene terephthalate. The materials of the release liner film and the carrier layer are preferably selected in such a way that the melting temperature of the said films lies below the decomposition temperature of the active substance present in the patch.

Advantageously, the release liner film and/or the carrier layer are provided with the active substance layer, and the layers, with the active substance layer, are put through a pair of heatable opposing rollers, which function as roller locks. In this process, the patch surface could be moulded as a heatable structure on the surface of one of the opposing rollers. One of both rollers can serve to create peripheral separating edges, particularly to separate individual patches from the layers. In contrast, the other of both rollers can bear the structure of the predetermined separating edge, e.g. in the form of an 'S-cut' or of a corresponding, similar opening aid. In this process, it is not necessary that both rollers are heatable. The roller for creation of a thermally effected peripheral separating edge can be heated, whilst the other roller for creation of the structure of the predetermined separating edge (e.g. the S-cut) is supposed to effect only a targeted weakening of the release liner film, and does not have to be heatable, if it does not come into contact with the active substance layer. It is preferable, however, that a roller for creation of a peripheral separating edge as a edge of the patch, as well as a roller for creation of a predetermined separating edge with a weakened and/or at least partly broken region, particularly as an opening aid for the patch, are heatable. Finally, it is also possible for both, a peripheral separating edge as an edge of the patch, as well as a predetermined separating edge with a weakened and/or at least partly broken region, are produced by a single roller, which is heatable, whereas an opposing counter roller can be unheated.

A further subject of the invention is a process for manufacturing of a transdermal patch, whereby an active substance layer with a poorly water soluble active substance, particularly with rotigotine and/or one of its pharmacologically acceptable salts as an active substance, most particularly preferred with the free base of rotigotine, is located between a release liner film and a carrier layer, wherein the process is characterised in such a way that the release liner film and/or the carrier layer are electrically discharged directly before the release liner film and/or the carrier layer is provided with a peripheral separating edge. Separation of the patches can particularly be carried out when the release liner film and/or the carrier layer being provided with the thermally effected peripheral separating edge. Due to the electrical discharge of the release liner film and/or the carrier layer, the risk of crystallisation of the active substance in the active substance layer can be further reduced. The term 'directly before the release liner film and/or the carrier layer is provided with a peripheral separating edge' here means that no further process step is used on the corresponding layer between the electrical discharge and provision with a peripheral separating edge, and that the layer does not cover unnecessary distance between the discharge and the provision with a peripheral separating edge. This has the advantage that between the discharge and providing the layer with a peripheral separating edge, a renewed charging of one of the layers cannot take place. For the discharge of the release liner film and/or the carrier layer directly before the separation or the provision of a peripheral separating edge, the voltage discharge can take place over a large-area electrical side, for example. For example the voltage can be discharged over carbon filaments or stainless steel wires. Preferably the voltage discharge is combined with the thermal separation process. In a preferred embodiment, therefore, the release liner film and the carrier layer are both electrically discharged in each case, and then provided in each case with a thermally effected peripheral separating edge, and connected to each other in such a way that they can be detached from each other, and that the intermediate layer containing the active substance is sealed.

In another preferred process for manufacturing of a transdermal rotigotine patch, the active substance is not in crystalline form. In another preferred process for manufacturing of a transdermal rotigotine patch, the active substance is in amorphous form. Preferably in the active substance layer rotigotine is essentially in the form of the free base, i.e. more than 90 mol % and in 5-20 wt %, relative to the weight of the active substance layer. In the rotigotine patch manufactured this way, also after being stored for 12 months at 25° C., preferably for 24 months at 25° C., no rotigotine crystals (e.g. form II) can be detected. The active substance being in amorphous form means that it essentially does not comprise any crystal structures.

The process according to the invention serves for the manufacturing of a transdermal patch, in which an active substance layer is located between a release liner film and a carrier layer, wherein the active substance layer contains a non-crystalline, poorly water soluble active substance, particularly rotigotine or one of its pharmacologically acceptable salts, and is essentially free from crystallisation nuclei of the active substance. In one embodiment, the active substance layer contains an amorphous, poorly water soluble active substance, particularly rotigotine or one of its pharmacologically acceptable salts. The release liner film and/or the carrier layer of the patch are provided with at least one thermally effected separating edge. The term 'essentially' expresses that crystal structures with up to less than 1 wt %, based on the respective active substance content used, are permitted to exist, without the active substance being denoted as being in an at least partly crystalline form.

The use of an above-described process for inhibiting the appearance of rotigotine crystals in the patch is also a subject of the invention.

A further subject of the invention is a tool for the manufacturing of a transdermal patch by the process as described above.

The tool comprises two opposing rollers, which are at least partly heatable, through which the release liner film and the carrier layer as well as the active substance layer can be passed. The active substance layer can be applied on the release liner film and/or the carrier layer. The term 'can be passed through' here means that the corresponding layer can be passed through between the two opposing rollers, which form a roller lock. At least one of both rollers is at least partly heatable, in order to thermally induce a separating edge of the patch. It is conceivable that the roller is only heatable in the area of a tool element, which is suitable for forming a peripheral separating edge. The geometry of the tool suitable for forming a peripheral separating edge, which acts as an sealing element for sealing the active substance layer, is particularly chosen in such a way that the flow direction of the active substance containing matrix is directed into the inside of the patch. This preferred design of the sealing element permits for longer cleaning intervals, longer maintenance intervals and/or lifecycle of the tool. In addition to the design of the tool with only one heatable tool element, it is also possible, however, that a roller is completely heatable, or that both rollers are partly or completely heatable. The corresponding parts of the roller or rollers are constructed in such a way that they can be heated to a desired temperature by electric resistance, which temperature is preferably above a melting temperature of an active substance crystal and/or above the sterilisation temperature of a certain nucleus. In the case of rotigotine, it is advantageous if at least the roller, which is designed for separating the patches, can be heated to at least 100° C., or to above 110° C. or above 120° C. If polypropylenes or polyethylene terephthalate films are used in the release liner film or carrier layer, it is advantageous to heat the tool elements, used for introducing the separating edges, to approximately 170° C. or approximately 260° C. and above. In addition, it is conceivable that more than two rollers are used for carrying out the above-described process for manufacturing of an patch as described above, for example, in the form of a sequential arrangement of several roller pairs opposing each other.

In a preferred embodiment, a first roller is used for separating the patch by at least one peripheral edge, and a second roller, opposing the first, is used for the formation of a weakened and/or at least partly broken region by a predetermined breaking edge. As described above, the separation of the patch is performed by a thermally effected peripheral cutting edge, which cuts the layers. The formation of the weakened and/or at least partly broken region as a predetermined separating edge preferably takes place in such a way, in contrast, that only the release liner film is weakened and/or at least partly broken, meaning that not all layers are cut. For this reason, the second roller designed for the manufacturing of the predetermined breaking edge can be designed in such a way that it does not induce the predetermined breaking edge thermally, but rather purely mechanically, for example, by cuts. However, in a preferred embodiment of the invention, the second roller can also be heated.

In addition to preferred rollers of this type, the tool can also be a punching device with a heated punching tool.

In a further preferred embodiment, the tool is suitable for separating a multitude of similar transdermal patches, based in each case on a sheet of a release liner film, a carrier layer and an active substance layer. This tool therefore serves for manufacturing of transdermal patches on an industrial scale, in which the separating edges are thermally effected. Due to the thermal creation of the separating edges, the development of nuclei, particularly of crystal nuclei, is directly avoided in manufacturing.

A further subject of the invention is the use of a tool according to the invention in carrying out the process according to the invention for the manufacturing of a transdermal patch according to the invention.

In the case of an above described transdermal patch, atmospheric influences promoting crystal growth on the patch edges, for example, by oxygen entry, water absorption, evaporation losses or contamination of the manufacturing plant by single 'seed' crystals in the 'form II' of rotigotine or of other active substance crystals are specifically prevented. Contamination of the separating tool with an active substance crystal, for example, with rotigotine 'form II', is prevented in the process according to the invention, which consequently prevents an otherwise subsequent contamination of the separating edge, which is created by the separating tool. Also, mechanical shear forces on the mechanically produced separating edges and/or electromechanical pulses when separating the patches, which are caused by voltage differences between the release liner film and the carrier layer, or other effects and a subsequent short circuit during mechanical separation, are also reliably avoided in a preferred process. Finally, crystal nuclei formation on surface defects of mechanically produced separating edges is avoided.

Accordingly, a transdermal patch is provided, which prevents or clearly reduces the development of crystals in the active substance layer of the patch.

The transdermal patches according to the invention are suitable for treatment of diseases. If rotigotine or one of its pharmaceutically acceptable salts as an active substance is comprised by the patch, the transdermal patches are particularly suitable for treating diseases which are accompanied by disorders of dopamine metabolism and/or disorders of the dopaminergic signalling cascade. Rotigotine is thus particularly suitable for treatment and/or prevention of a disease selected from the group of Parkinson-Plus depression fibromyalgia, as well as particularly Parkinson's disease, and Restless Leg Syndrome.

A further subject of the invention is therefore the use of a patch, as described above and as described in the claims, wherein the active substance is rotigotine or one of its pharmacologically acceptable salts, and particularly the free base is rotigotine, for manufacturing of a pharmaceutical for prevention and/or treatment of a disease selected from Parkinson-Plus, depression, fibromyalgia, as well as, preferably, Parkinson's disease and Restless Leg Syndrome.

Further advantages and preferred embodiments are can be seen from the claims and the following description of the examples.

SHORT DESCRIPTION OF THE FIGURES

EXAMPLES

Example 1

Using a hot wire, a smaller patch was cut out of a crystal-free portion of a patch containing rotigotine, in which crystal growth could already be seen on the cutting edges. In the process, the hot wire was part of a polystyrene cutting machine. The opposite-facing surfaces of the patch, thus the release liner film and the carrier layer, were thermally bonded to each other. The patch was stored at different temperatures, namely 1 week at ca. 4° C. and subsequently ca. 10 months at room temperature. This thermally effected separating edge of the patch showed no crystal growth after an optical inspection of the edge.

Example 2

Figure 1:
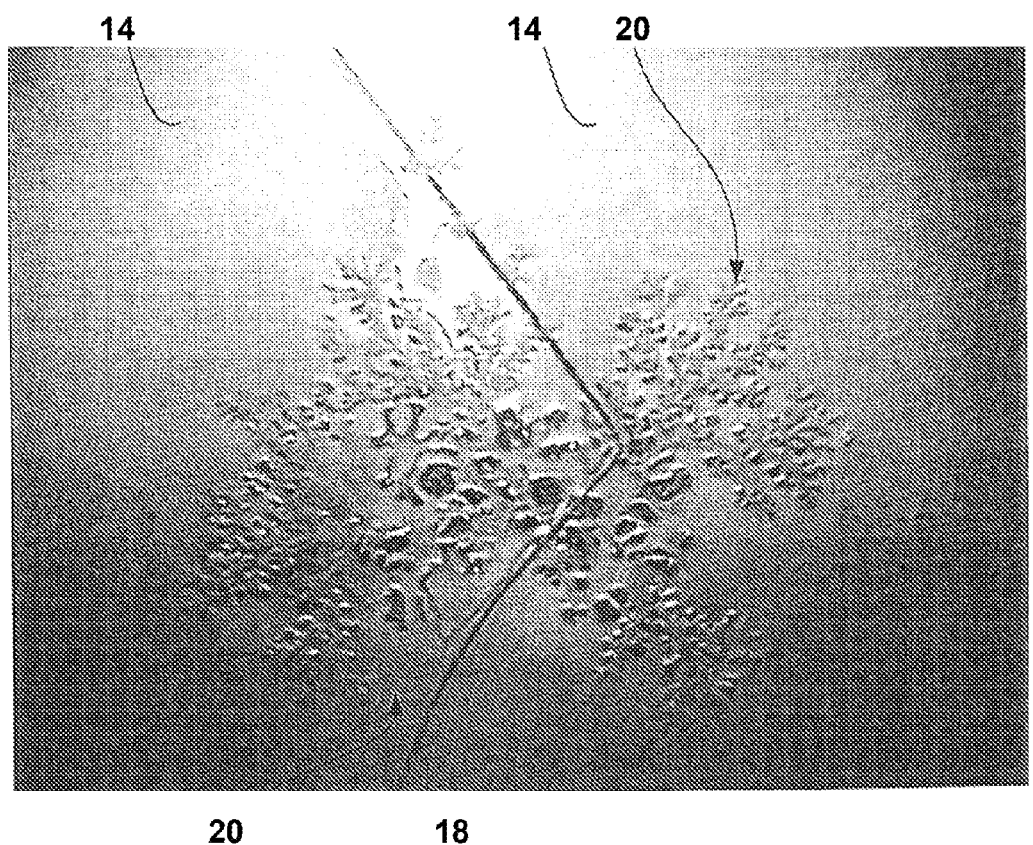
FIG. 1 shows a photo of a transdermal patch from the prior art, wherein crystal growth in the active layer can be seen along a separating edge.
Figure 2:
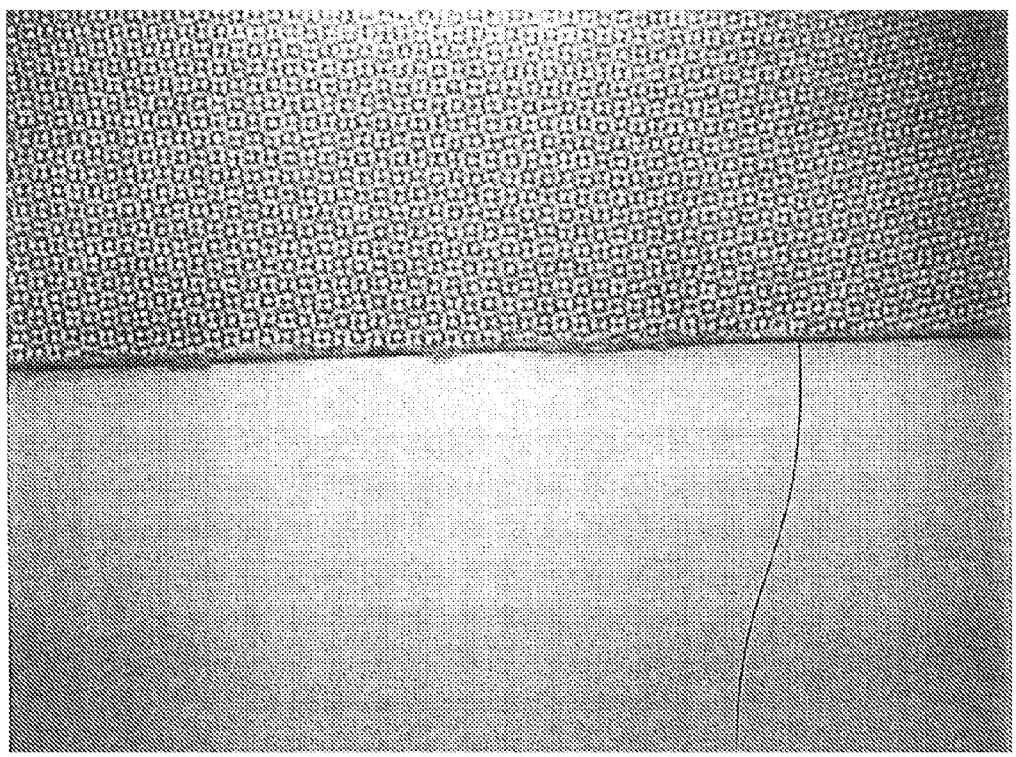
FIG. 2 shows a photo of a transdermal patch according to the invention with a thermally effected separating edge without crystal growth in the active substance layer.

Using a conventional film welding device, a smaller patch was released from a crystal-free portion of a patch containing rotigotine, in which crystal growth could already be seen on the cutting edges. In the process, the opposite-facing surfaces of the patch, thus the release liner film and the carrier layer, were thermally bonded to each other. The patch was stored at different temperatures, namely 1 week at ca. 4° C. and subsequently ca. 10 months at room temperature. FIG. 2 shows a photo in 10fold magnification of the patch treated in this way after the storage as described above. It can clearly be seen that no crystal growth on the separating edge 18 can be detected by optical inspection.

Comparative Example 1

Figure 3:
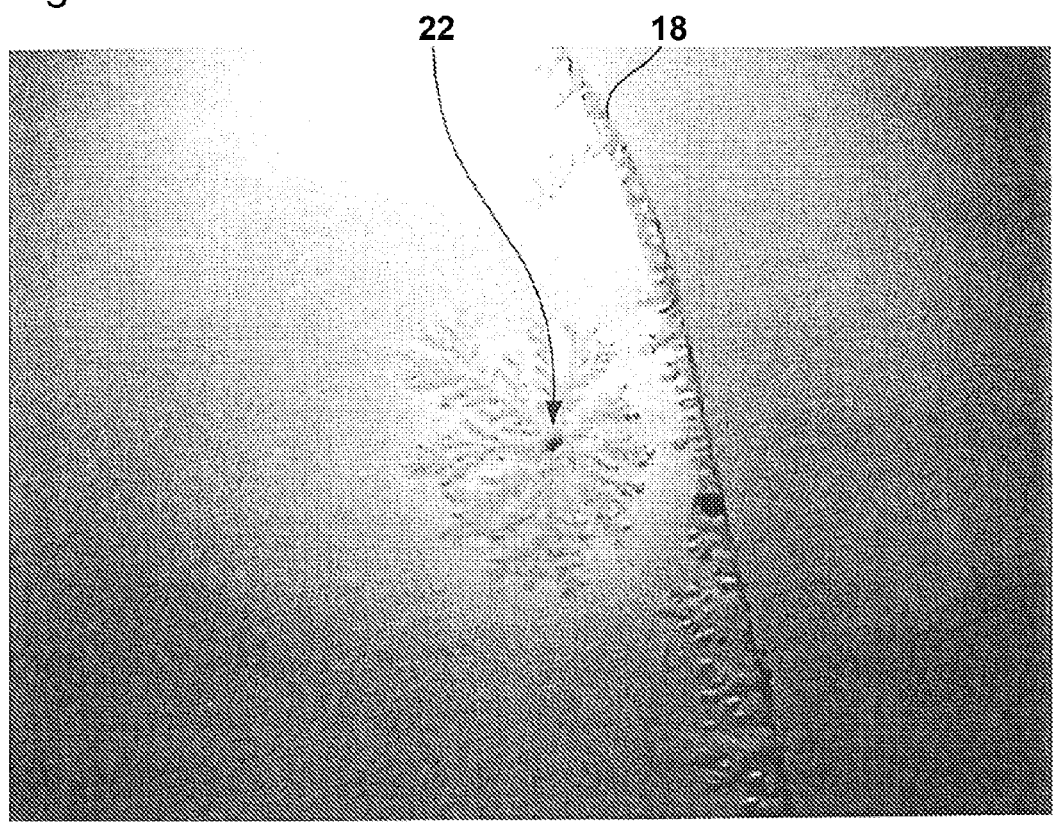
FIG. 3 shows a photo of a transdermal patch, which has been provided with a separating edge according to the comparative example 1, and shows crystal growth.

In a crystal-free portion of a patch containing rotigotine, a new separating edge was created with household scissors. The environment of this separating edge was exposed to electric fields, namely ca. 10,000V with a high-voltage generator, in order to investigate the influence of electric charges on the layers on the crystal growth. The patch was stored at room temperature for two weeks. As can be seen in FIG. 3, which shows a photo of this separating edge, in evidence visible crystal growth can be observed on the separating edge 18 as well as on the point 22 exposed to the spark gap.

Example 3

Figure 4:
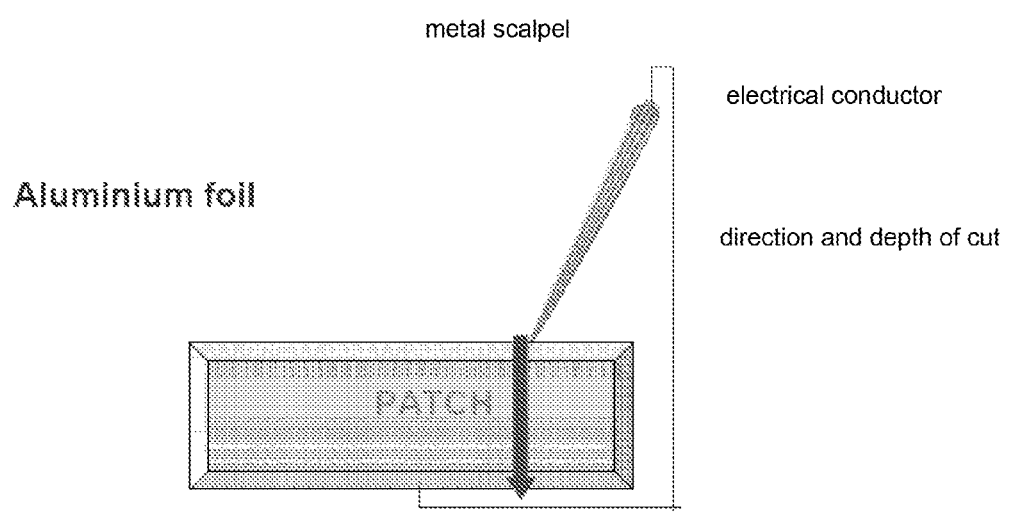
FIG. 4 shows an experimental sketch for manufacturing of a transdermal patch according to the invention, in which the voltage differences are equalised/discharged, i.e. the voltage discharge of the release liner film and/or carrier layer takes place.
Figure 5:
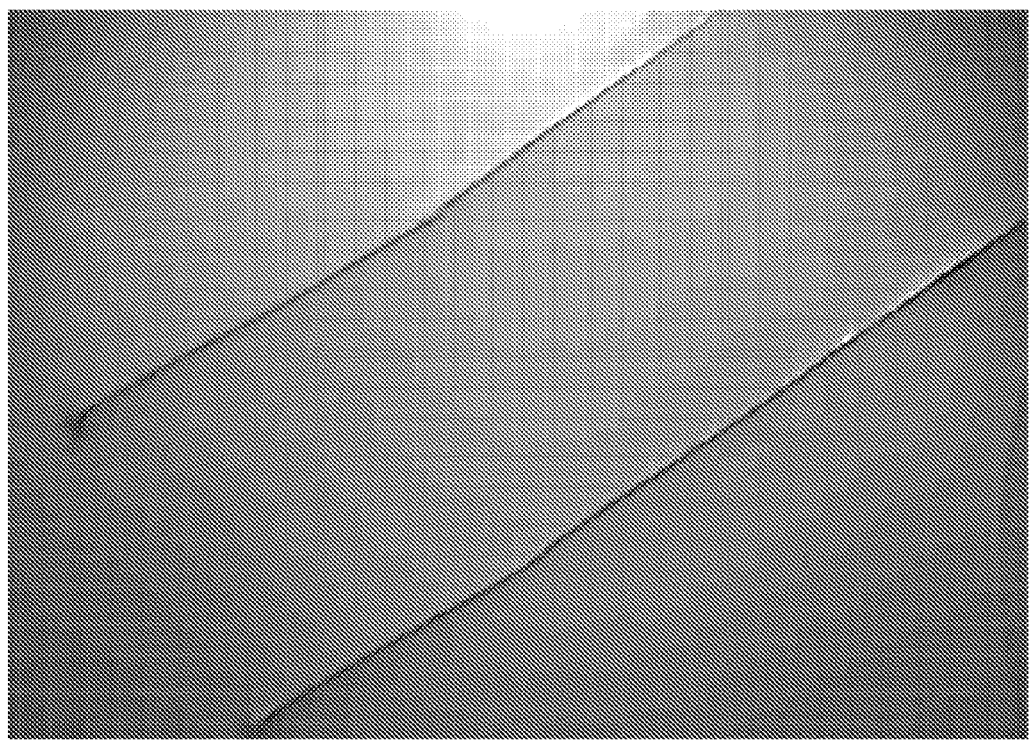
FIG. 5 shows a photo of a transdermal patch with a cutted separating edge, in which the voltage discharge of the release liner film and/or carrier layer has been taken place during the manufacturing of a separating edge/predetermined breaking edge, without crystal growth in the active substance layer.

A patch containing rotigotine was completely wrapped in aluminium foil and subsequently electrically connected via a potential equalisation cable with a scalpel made of metal (FIG. 4). The patch covered in aluminium was sliced through in several places with the scalpel which is electrically neutralised in this way. The patch was stored at room temperature for 2 months. FIG. 5 shows a photo of the patch treated in this way after 2 months. It can clearly be seen that no crystal growth on the separating edge 18 can be detected by optical inspection.

Comparative Example 2

Figure 6:
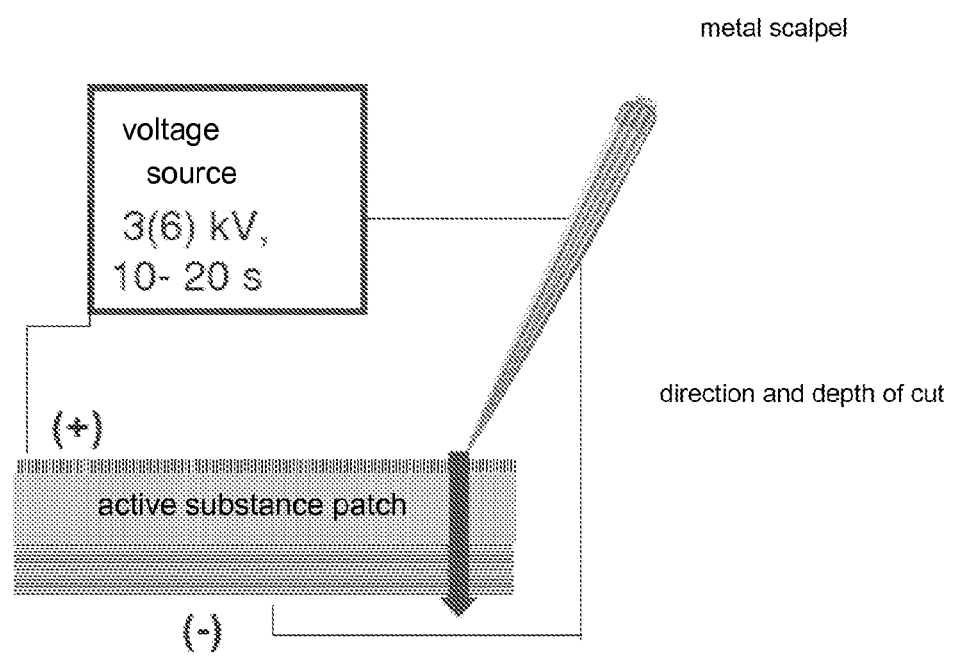
FIG. 6 shows an experimental sketch according to the comparative example 2 for manufacturing of a transdermal patch according to the invention, in which the voltage differences have been established and not equalised/discharged, i.e. the voltage discharge of the release liner film and/or the carrier layer does not take place. (The cutting tool (scalpel) is not connected to the conductors).
Figure 7:
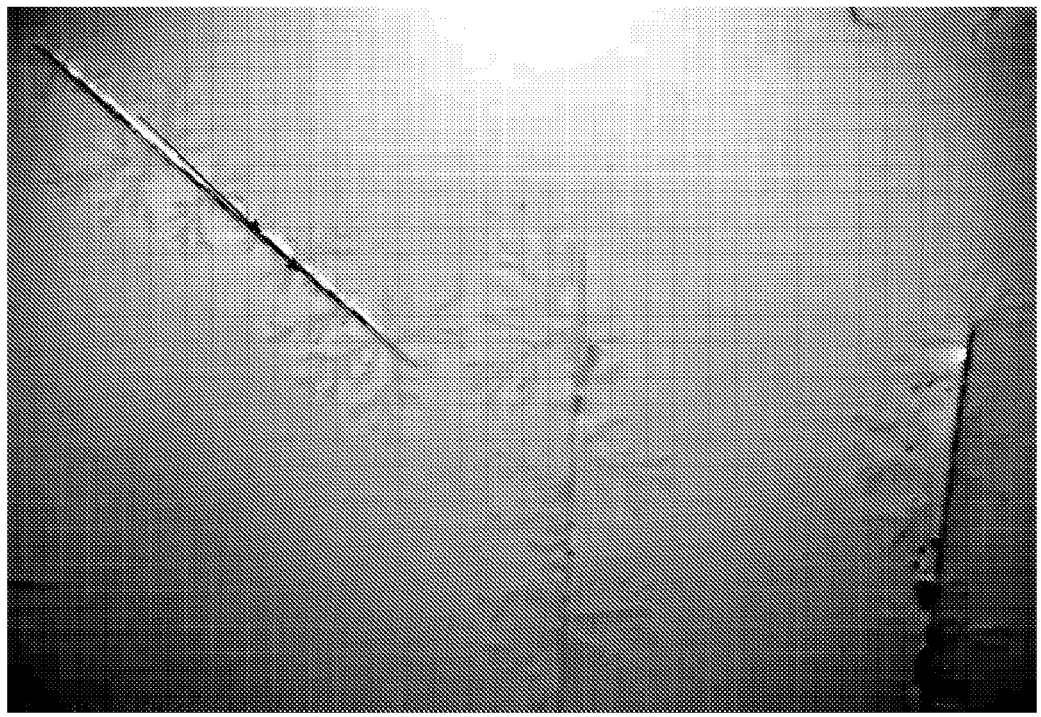
FIG. 7 shows a photo of a transdermal patch, which is provided with a separating edge according to the comparative example 2, and which shows crystal growth.

The films of a crystal-free patch containing rotigotine were electrically charged by applying a voltage of ca. 3 kV (FIG. 6). Subsequently, the patch was sliced through by means of an electrically grounded scalpel, and then stored at room temperature for 1 month. As can be seen from FIG. 7, which shows a photo of this separating edge (cutting line) after storage at room temperature for 1 month, a clearly visible crystal growth 20 can be observed on the separating edge 18.

Comparative Example 3

Figure 8:
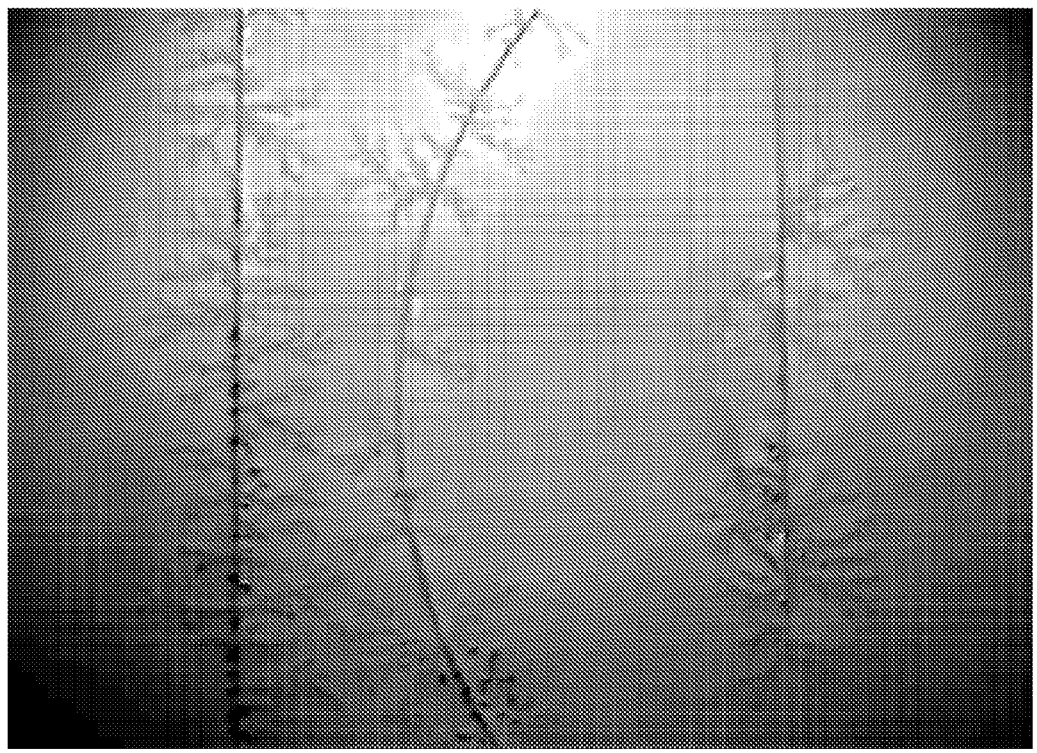
FIG. 8 shows a photo of a transdermal patch, which is provided with a separating edge according to the comparative example 3, and which shows crystal growth.

A crystal-free, transdermal patch containing rotigotine, which was already provided with a punching line (e.g. S-cut) 24 before the treatment, was fixed with the release liner side downwards on a polystyrene plate by means of adhesive tape. The free carrier layer side of the patch, not lying on the polystyrene plate, was electrostatically charged with a natural bristle brush (flat brush, ca. 2 cm wide) by one-dimensional friction (over 10 sec) at normal humidity and room temperature. Subsequently, the patch was sliced through in several places as in example 3 by means of an electrically grounded scalpel. The patch treated in this way was stored at room temperature for 1 month. FIG. 8 shows a photo, in which a clear crystal development 20 can be observed along the cutting edges 18. In addition, a crystallisation 20 was observed in the punching line (S-cut) 24, already present in the patch before treatment.

The invention claimed is:

1. A transdermal patch, comprising
a release liner film,
a polymer layer containing a non-crystalline active substance, and
a carrier layer,
wherein the active substance layer is between the release liner film and the carrier layer,
the release liner film and/or the carrier layer comprising at least one peripheral separating edge with none of the polymer layer therebetween,
wherein the release liner film and the carrier layer are thermally and detachably directly connected to each other over a length of at least 70% of the peripheral separating edge, such that the polymer layer is sealed by said thermally and detachably connected peripheral separating edge.

2. The transdermal patch according to claim 1, wherein the detachable connection of the peripheral edge is created by a thermal process selected from the group consisting of welding, thermal caulking and/or thermal joining.

3. The transdermal patch according to claim 1, wherein the active substance is selected from the group consisting of rotigotine, a pharmacologically acceptable salt of rotigotine, and the free base of rotigotine.

4. The transdermal patch according to claim 1, wherein the polymer layer comprises a silicone-based adhesive.

5. The transdermal patch according to claim 1, in which at least the release liner film comprises a weakened and/or breakable region, which weakened and/or breakable region can be used as an opening aid for the patch.

6. The transdermal patch according to claim 1, in which release liner film and carrier layer are made from the same material.

7. The transdermal patch according to claim 1, in which the release liner film has a thickness in the range of about 50-150 µm.

8. The transdermal patch according to claim 3, wherein rotigotine is present in the active substance layer essentially in the form of the free base and in 5-20 wt %, relative to the weight of the active substance layer.

9. The transdermal patch according to claim 1 for treatment of a disease selected from the group consisting of Parkinson's disease, Restless Leg Syndrome, Parkinson-Plus, depression and fibromyalgia.

10. The transdermal patch of claim 3 in which no crystals of rotigotine form II can be detected.

11. The transdermal patch of claim 1 wherein said at least one peripheral separating edge is a peripheral edge of said patch.

12. A method for the treatment of a disease, selected from the group consisting of Parkinson-Plus, depression, fibromyalgia, as well as Parkinson's disease and Restless Leg Syndrome, the method comprising the application to a patient in need thereof of a transdermal patch according to claim 1,
wherein the release liner film and the carrier layer are thermally and detachably connected to each other over a length of at least 70% of the peripheral separating edge, such that the polymer layer is sealed by said thermally and detachably connected peripheral separating edge.

13. A process for manufacturing a transdermal patch according to claim 1, the process comprising
a) providing a release liner film and a carrier layer;
b) providing an active substance layer comprising an active substance selected from rotigotine, rotigotine free base, and/or one of its pharmacologically acceptable salts, said active substance layer being disposed between said release liner film and said carrier layer, wherein the release liner film and/or the carrier layer of the patch is provided with at least one thermally effected peripheral separating edge,
thermally and detachably bonding the release liner film and the carrier layer directly to each other along at least 70% of the peripheral separating edge, such that the active substance layer is sealed by the thermally bonded peripheral separating edge.

14. The process according to claim 13, wherein the release liner film is thermally weakened and/or at least partly broken in a region of a predetermined breaking edge, which predetermined breaking edge can be used as an opening aid for the patch.

15. The process according to claim 13, wherein the thermal bonding is carried out above a melting temperature of an active substance.

16. The process according to claim 13, wherein the thermal bonding is accomplished by means of a pair of heatable opposing rollers.

17. The process according to claim 13, wherein the release liner film and the carrier layer are electrically discharged directly before the release liner film and/or the carrier layer are provided with a thermally effected separating edge.

18. The process according to claim 13, wherein the active substance is in amorphous form.

19. The process of claim 18 wherein the appearance of rotigotine crystals in the patch is eliminated.

* * * * *